(12) United States Patent
Schewe et al.

(10) Patent No.: US 9,597,155 B2
(45) Date of Patent: Mar. 21, 2017

(54) RADIOPAQUE MATERIAL FOR ENHANCED X-RAY ATTENUATION

(71) Applicant: BOSTON SCIENTIFIC SCIMED, INC., Maple Grove, MN (US)

(72) Inventors: Scott R. Schewe, Eden Prairie, MN (US); Benjamin P. Gundale, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 113 days.

(21) Appl. No.: 14/180,229

(22) Filed: Feb. 13, 2014

(65) Prior Publication Data

US 2014/0277393 A1    Sep. 18, 2014

Related U.S. Application Data

(60) Provisional application No. 61/777,865, filed on Mar. 12, 2013.

(51) Int. Cl.
  *A61F 2/82*  (2013.01)
  *A61B 19/00*  (2006.01)

(52) U.S. Cl.
  CPC .......... *A61B 19/54* (2013.01); *A61B 90/39* (2016.02); *A61B 2090/3966* (2016.02); *A61F 2/82* (2013.01); *A61F 2250/0098* (2013.01)

(58) Field of Classification Search
  CPC .............................. A61F 2250/0098
  See application file for complete search history.

(56) References Cited

U.S. PATENT DOCUMENTS

| | | | | |
|---|---|---|---|---|
| 6,262,142 B1 * | 7/2001 | Wang | ............ | A61K 6/083 523/113 |
| 6,309,420 B1 * | 10/2001 | Preissman | .......... | A61B 17/7095 424/423 |
| 6,916,354 B2 | 7/2005 | Elliott | | |
| 7,951,093 B2 | 5/2011 | Skujins et al. | | |
| 8,137,293 B2 | 3/2012 | Zhou et al. | | |
| 9,265,866 B2 * | 2/2016 | Kramer-Brown | ....... | A61L 31/08 |
| 2005/0211930 A1 * | 9/2005 | DeMeo | ............ | G01V 5/0008 250/516.1 |
| 2008/0058919 A1 | 3/2008 | Kramer-Brown et al. | | |

(Continued)

OTHER PUBLICATIONS

Brouwers, H.J.H., "Particle-size Distribution and Packing Fraction of Geometric Random Packings," Physical Review E, vol. 74(3): 031309-1-031309-14, Sep. 26, 2006.

*Primary Examiner* — Katrina Stransky
*Assistant Examiner* — Wade P Schutte
(74) *Attorney, Agent, or Firm* — Seager, Tufte & Wickhem, LLP

(57) ABSTRACT

A medical device that may be implanted in a patient's body is disclosed. An illustrative medical device has an elongated structure that includes a material loaded with a radiopaque material. The radiopaque material includes radiopaque particles having multiple sets of radiopaque particles. The multiple sets of radiopaque particles may include a first set of radiopaque particles having particles with particle sizes in a first particle size range and a second set of radiopaque particles having particles with particle sizes in a second particle size range. The second set of radiopaque particles may have particles configured to fit within interstitial spaces between particles of the first set of radiopaque particles.

16 Claims, 7 Drawing Sheets

(56) References Cited

U.S. PATENT DOCUMENTS

2010/0191318 A1 7/2010 Stinson et al.
2011/0130822 A1* 6/2011 Cottone .................... A61F 2/91
   623/1.15

* cited by examiner

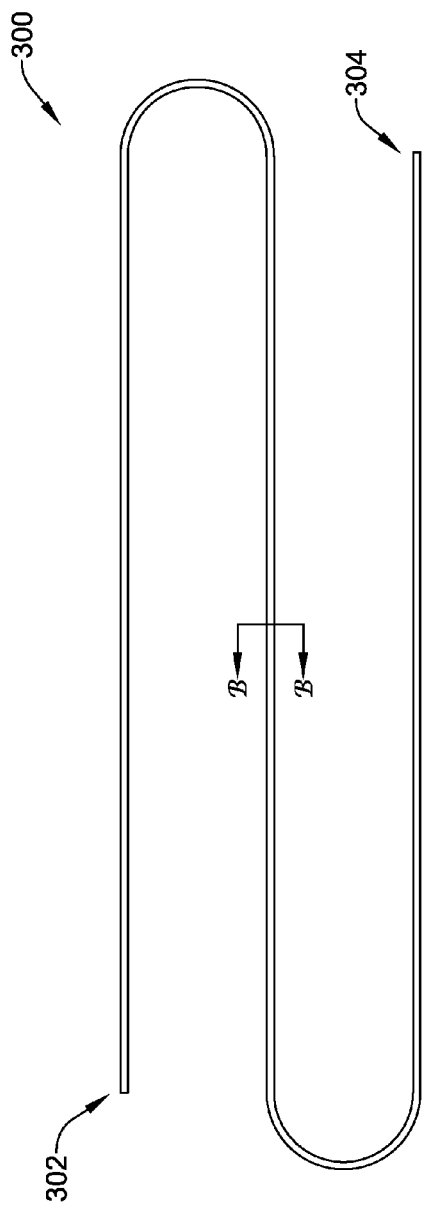
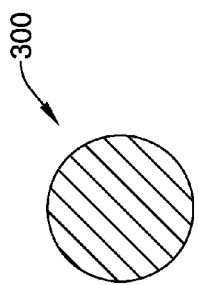

RADIOPAQUE MATERIAL FOR ENHANCED X-RAY ATTENUATION

CROSS-REFERENCE TO RELATED APPLICATIONS

This application claims priority under 35 U.S.C. §119 to U.S. Provisional Application Ser. No. 61/777,865, filed Mar. 12, 2013, the entirety of which is incorporated herein by reference.

TECHNICAL FIELD

The present disclosure relates generally to implantable medical devices. In particular, the invention relates to implantable medical devices having radiopaque material, and a method of making thereof.

BACKGROUND

Implantable medical devices, such as catheters, guidewires, stents, etc. are widely used in procedures ranging from diagnostic evaluations to angioplasty, deployment of stents in the coronary arteries, and other medical procedures. During such procedures, a practitioner may need to know the position of the medical device during its positioning in a patient's body. For this purpose, a radiopaque material is sometimes affixed on the surface or incorporated in the material of the implantable medical device.

Using techniques such as fluoroscopy, real-time images of the location or orientation of medical devices in a patient body can be viewed or obtained using X-rays. To obtain bright and clear real-time images, the radiopaque material must have sufficient radiopacity, e.g., the ability of the material to absorb X-rays or high attenuation of X-ray energy to produce a high contrast fluoroscopic image. Thus, a device with a radiopaque material exhibits high attenuation of X-ray energy and can be seen with high contrast in the fluoroscopic image of the device. The radiopacity of a material depends on its composition.

SUMMARY

Although medical devices comprised of and/or comprising radiopaque materials exist, a need for developing medical devices with radiopaque materials that are stable, economical, and exhibit sufficient attenuation of x-ray energy is needed.

In one aspect, the present disclosure provides a medical device having an elongated structure. The elongated structure may include a biocompatible material that is loaded with a radiopaque material or has a radiopaque material applied thereto. The radiopaque material may include radiopaque particles having sets of radiopaque particles with particles having different particle size ranges. The radiopaque particles having sets of particles with different particle size ranges may form a multimodal (e.g., bimodal, trimodal, etc.) distribution or other type of distribution.

In another aspect, the present disclosure provides a method of manufacturing a medical device. The method may involve mixing at least two different sets of radiopaque particles, one or more of which has particles of a particular size range that differs from one or more sets of the at least two different sets of radiopaque particles.

In another aspect, the present disclosure provides a medical device having an elongate shaft. The elongate shaft may have a marker band with a radiopaque material. The radiopaque material may include two sets of radiopaque particles—a first set and a second set. The first set of radiopaque particles may include particle sizes within a first range of particle sizes and the second set of radiopaque particles may include particle sizes within a second range of particle sizes. The second range of particle sizes may have an upper limit that is less than a lower limit of the first range of sizes.

In another aspect, the present disclosure provides a stent having a body. The body of the stent may include a polymer that is loaded with a radiopaque material. The radiopaque material may include radiopaque particles having a bimodal particle size distribution.

In yet another aspect, the present disclosure provides a medical device having a structure with a radiopaque material. The radiopaque material may include two sets of radiopaque particles—a first set and a second set. The first set of radiopaque particles may have particle sizes within a first range of particle sizes and the second set of radiopaque particles may have particle sizes within a second range of particle sizes. The second range of particle sizes may have an upper limit that is less than a lower limit of the first range of sizes.

The above summary of exemplary embodiments is not intended to describe each disclosed embodiment or every implementation of the present disclosure.

BRIEF DESCRIPTION OF THE DRAWINGS

The disclosure may be more completely understood in consideration of the following detailed description of various embodiments in connection with the accompanying drawings, in which:

FIG. 4A is a schematic side view of an illustrative medical device according to an aspect of this disclosure;

FIG. 4B is a schematic cross-sectional view of the illustrative medical device of FIG. 4A taken along line B-B according to an aspect of this disclosure;

Figure 1:
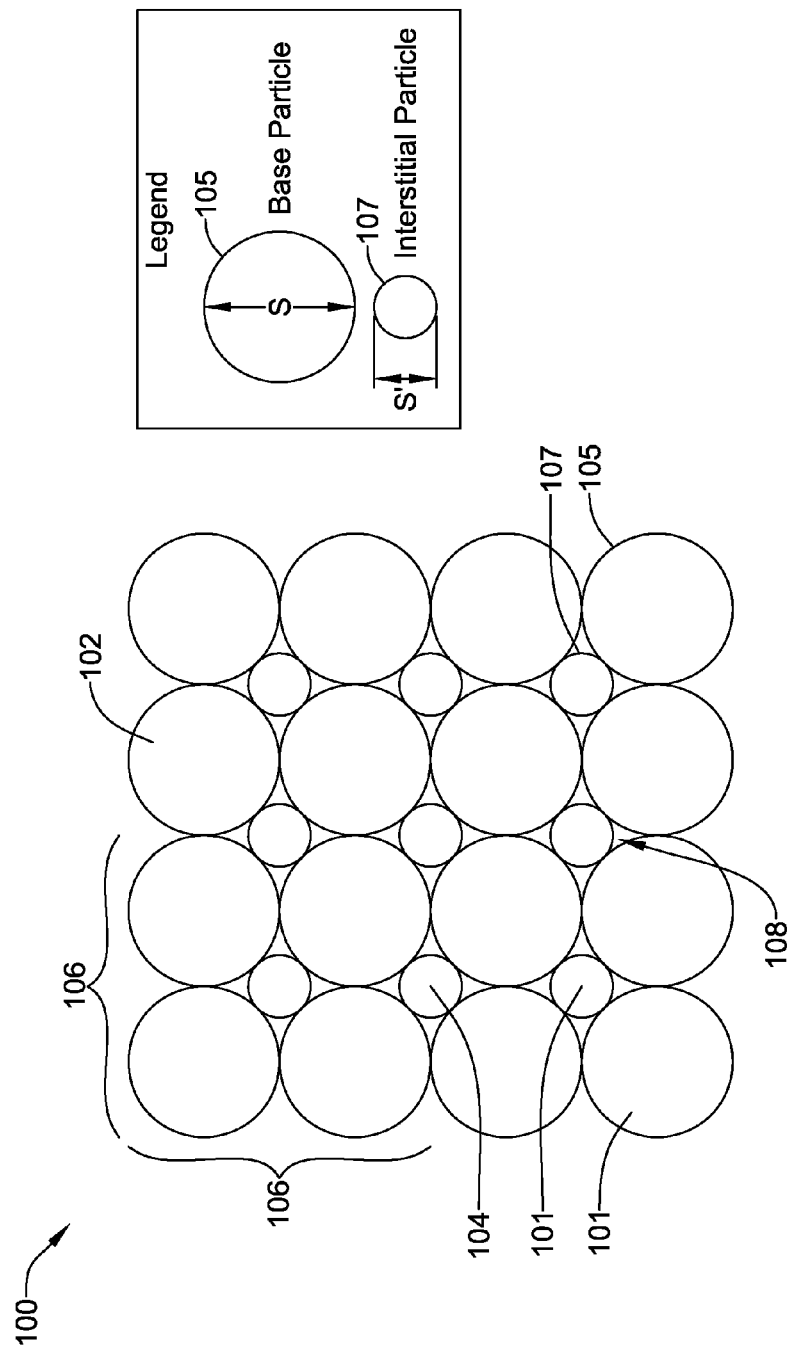
FIG. 1 is a schematic view of an illustrative packing structure of material with a bimodal particle size distribution according to an aspect of this disclosure.

While the disclosure is amenable to various modifications and alternative forms, specific illustrations thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may be indicative as including numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

Although some suitable dimensions, ranges, and/or values pertaining to various components, features, and/or specifications are disclosed, one of ordinary skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end further from the device operator during use.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

It is noted that references in the specification to "an embodiment", "some embodiments", "other embodiments", "some instances", "some cases", etc., indicate that the embodiment or instance described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with one embodiment, it should be understood that such feature, structure, or characteristic may also be used in connection with other embodiments whether or not explicitly described unless clearly stated to the contrary.

During implantation and monitoring of medical devices, such as stents, catheters, guidewires, etc. in a patient's body, a practitioner may need to know a particular location and/or orientation of the medical device. Medical imaging techniques, such as fluoroscopy may be used to view real-time images of a medical device that has been implanted or that will be implanted in a patient's body using X-rays. For this purpose, radiopaque material may be fixed on the surface of the medical device and/or incorporated into the material of the medical device. The brightness and clarity of real-time images of medical devices incorporating radiopaque material depends upon a radiopacity of the radiopaque material of the medical device. The radiopacity of a material may be defined as the ability of the material to obstruct the passage of radiant energy (e.g., X-rays) and produce a high contrast fluoroscopic image. In some instances, the density of a material may determine the material's radiopacity. Generally, if the material is more dense, the attenuation of the X-ray energy by the material of the medical device is enhanced, thereby producing a clearer and brighter real-time image of the medical device.

Conventional implantable medical devices with the radiopaque material typically have radiopaque particles having particle sizes within a single particle size range (e.g., particle sizes having a unimodal distribution). Radiopaque material of medical devices typically includes radiopaque particles with particle sizes of approximately uniform size, where the radiopaque material may include relatively large interstitial spaces between these particles when the radiopaque particles are in a packed structure. Even so, it is contemplated that radiopaque materials may have radiopaque particles with some variation in particles sizes due to limitations in manufacturing techniques and tolerances, aggregation of particles, etc. Thus, the particle sizes in a radiopaque material having a unimodal distribution may vary by a particular percentage of the mode (e.g., substantially all of the particles of the radiopaque material may have particle sizes within 10% of the particle size mode for the radiopaque material) or by a certain number of standard deviations from a mean (e.g., when the unimodal distribution is a normal distribution, etc.), or by some other statistical measurement.

In some illustrative aspects, the disclosed concept may incorporate radiopaque materials 100 having multiples sets of radiopaque particles 101 with each set of radiopaque particles 101 having different particle size ranges. In some instances, one or more sets of radiopaque particles 101 may be sized to fill interstitial spaces 108 between radiopaque particles 101 of a set of radiopaque particles 101 having a larger particle size range. It has been found that filling interstitial spaces 108, to a degree, may increase a density of the radiopaque material 100, which may lead to enhanced attenuation of X-ray energy as compared to that of radiopaque materials having a unimodal distribution of the radiopaque particle sizes. Illustratively, as shown in FIG. 1, a first set 102 of particles 101 (referred to as base particles 105) that may have particle sizes S larger than particle sizes S' of a second set 104 of the particles 101 (referred to as interstitial particles 107), where the particles 101 second set 104 of particles 101 may be configured to fill the interstitial spaces 108 between the base particles 105.

The interstitial particles 107 may have any particle size configured to fit within the interstitial spaces 108 of the base particles 105. It has been found, however, that some particle sizes are more desirable than other particle sizes. For example, it has been determined that although several nano-scale sized radiopaque particles may be capable of more closely filling interstitial spaces 108 between base particles 105 than micro-sized radiopaque particles, use of nano-scale sized particles in radiopaque materials does not necessarily result in the X-ray attenuation improvement expected when compared to using micro-sized particles. This result appears to be because the overall density of the material with the nano-scale sized particles may not increase linearly with the decrease in particle sizes due to the use of nano-scale sized particles increasing the total number of particles in the radiopaque material 100, which increases the surface area capable of forming oxide (e.g., a low density material) thereon. In general, when radiopaque material, such as tungsten or other radiopaque material of a medical device, comes in contact with air or with blood in the tissue of the patient's body, an oxide layer may form on the surface of the material, which may ultimately decreases the overall density of the radiopaque material 100 of the medical device. This decrease in density of the radiopaque material 100 may reduce the attenuation of X-ray energy by the radiopaque material 100 and thus, reduce the effectiveness of the radiopaque material 100.

In this disclosure, for example, nano-scale sized particles may be defined as particles with sizes less than about 100 nanometers (nm). Generally, nano-scale sized particles may be particles with particles sizes between about 1 nm and about 100 nm, and micro-scale sized particles may be particles with sizes between 200 nm and 100 microns.

In some instances, the radiopaque material 100 may have radiopaque particles 101 that belong to three or more different particle size ranges (e.g., where each particle size range may have a unimodal particle size distribution that may be combined to form a trimodal distribution or larger distribution of particle sizes). It is contemplated that use of three or more different particle size ranges may be advantageous in at least situations where sizes of the interstitial spaces 108 between base particles (e.g., the particles of the set of particles having the largest particle sizes) may vary, as well as being advantageous in other situations. Thus, two or more additional sets of radiopaque particles 101 may be helpful in effectively filling the interstitial spaces 108.

FIG. 1 illustrates a schematic view of an illustrative radiopaque material 100. In this example, the radiopaque material 100 includes a plurality of radiopaque particles generally bearing reference number 101. The radiopaque particles 101 may be divided into two sets including a first set (generally bearing reference number 102) and a second set (generally bearing reference number 104). The first set 102 of radiopaque particles 101 may include a plurality of base particles 105. The second set 104 of radiopaque particles 101 may include a plurality of interstitial particles 107. The interstitial particles 107 may have particle sizes S' smaller than the particle sizes S of the base particles 105.

The first set 102 of the radiopaque particles 101 may include base particles 105 of approximately uniform size, arranged in a matrix of different dimensions, for example, the matrix may have the size of 2×2 (e.g., two columns by two rows), 2×3, 3×3, 3×4, 4×4, 10×10, 100×100, 100×1000, etc. Herein, the term "matrix" may refer to an array of columns and rows, where the radiopaque particles are arranged in a closely-packed structure. In the radiopaque material 100, four particles 105 of the first set 102 of radiopaque particles 101 may form a unit matrix 106 and an interstitial space 108 may be created between the four particles 105 of the unit matrix 106. The term "interstitial space" 108 may be defined as a void or an empty space surrounded by four particles arranged in a matrix of 2×2 dimensions or as any void or space at least partially between any number of particles 101, for example.

Alternatively, or in addition, to the radiopaque particles 101 of the radiopaque material 100 being in a matrix form, each base particle 105 of the first set 102 may be positioned adjacent to four other base particles 105, or any other number of base particles.

In some illustrative cases, the first set 102 of radiopaque particles 101 may have a particle size range spanning from about 5 microns to about 12 microns, 6 microns to 12 microns, 5 microns to 10 microns, 5 microns to 15 microns, or any other similar range of particle sizes. The second set 104 of radiopaque particles 101 may have a particle size range spanning from about 0.5 microns to about 4 microns, 0.6 microns to 3 microns, 0.7 microns to 4 microns, 1 micron to 4 microns, or any other similar range of particle sizes. In addition, or alternatively, the first set 102 of the radiopaque particles 101 may have a first particle size mode, median, and/or mean and the second set 104 of the radiopaque particles may have a second particle size mode, median and/or mean. In such instances, the particle size mode, median or mean, and/or particle size range of the second set 104 of radiopaque particles 101 may be configured (e.g., chosen) to fit in interstitial spaces 108 between the radiopaque particles 101 of the first set 102.

Alternatively, or in addition, the first set 102 of radiopaque particles 101 may have first particle sizes and the second set 104 of the radiopaque particles 101 may have second particle size that are approximately 10% to 35%, 15% to 35%, 10% to 30%, or other percentage range of the size of the first particle sizes. For example, if the first set 102 of radiopaque particles 101 has a particle size mode of 8.5 microns, then a particle size mode of the second set 104 of the radiopaque particles 101 may have particle sizes in the range of about 0.85 microns (10% of 8.5 microns=0.85 microns) to about 2.975 microns (35% of 8.5 microns=2.975 microns).

In some cases the second set 104 of radiopaque particles 101 may have a particle size mode having an upper limit less than a lower limit of a first range of particles sizes. For example, if the first set 102 of radiopaque particles 101 have particle sizes in the range from about 5 to about 12 microns, a first particle size mode may have a lower limit of 5 and an upper limit of 12. In a similar example, if the second set 104 of radiopaque particles have particle sizes in the range from about 0.7 microns to about 4 microns, a second particle size mode may have a lower limit of 0.7 microns and an upper limit of 4.

Further, the radiopaque particles 101 of the first set 102 may be mixed with the radiopaque particles 101 of the second set 104 to form a mixture. In some instances, the mixture may constitute about 60% to 90%, 65% to 90%, 70% to 90%, 60% to 95%, 65% to 95%, 70% to 90%, or other similar range by weight of the first set 102 of the radiopaque particles 101 and about 10% to 40%, 10% to 35%, 10% to 30%, 5% to 40%, 5% to 35%, 10% to 30%, or other similar range by weight of the second set 104 of the radiopaque particles 101. An illustrative mixture of radiopaque particles 101 may comprise 87% by weight of the first set 102 of the radiopaque particles 101 and 13% by weight of the second set 104 of the radiopaque particles 101. Illustratively, the formulation of the mixture may be optimized such that the mixture may be stable and may have a desired X-ray attenuation.

In some cases, the radiopaque particles 101 of the first set 102 and the radiopaque particles 101 of the second set 104 may form a multimodal particle size distribution. In some instances, the radiopaque particles of the first set 102 and the radiopaque particles of the second set 104 may have a bimodal particle size distribution, trimodal particle size distribution, etc. The term "multimodal distribution", as used in this disclosure and commonly understood, may mean a feature has a distribution having multiple modes and the term "bimodal distribution" may refer to a feature having a distribution with two modes. For example, radiopaque particles having a bimodal particle size distribution may have a first set 102 of particles 101 having a first particle size mode with a unimodal particle size distribution and a second set 104 of particles 101 having a second particle size mode with a unimodal particle size distribution, where the first and second set 102, 104 of particle sizes may be combined to form a mixture bimodal distribution with two modes.

Although it may be desirable to have distributions of particle sizes in each set of particles 101 that have small standard deviations from the mode, mean, and/or median of the particle set and thus, separate and distinct particle size ranges, it is contemplated that particle sizes in each particle set may overlap due to limitations of manufacturing tolerances and other similar and dissimilar factors. Such overlapping particle size ranges of the radiopaque particles may form a continuous bimodal particle size distribution.

Figure 2:
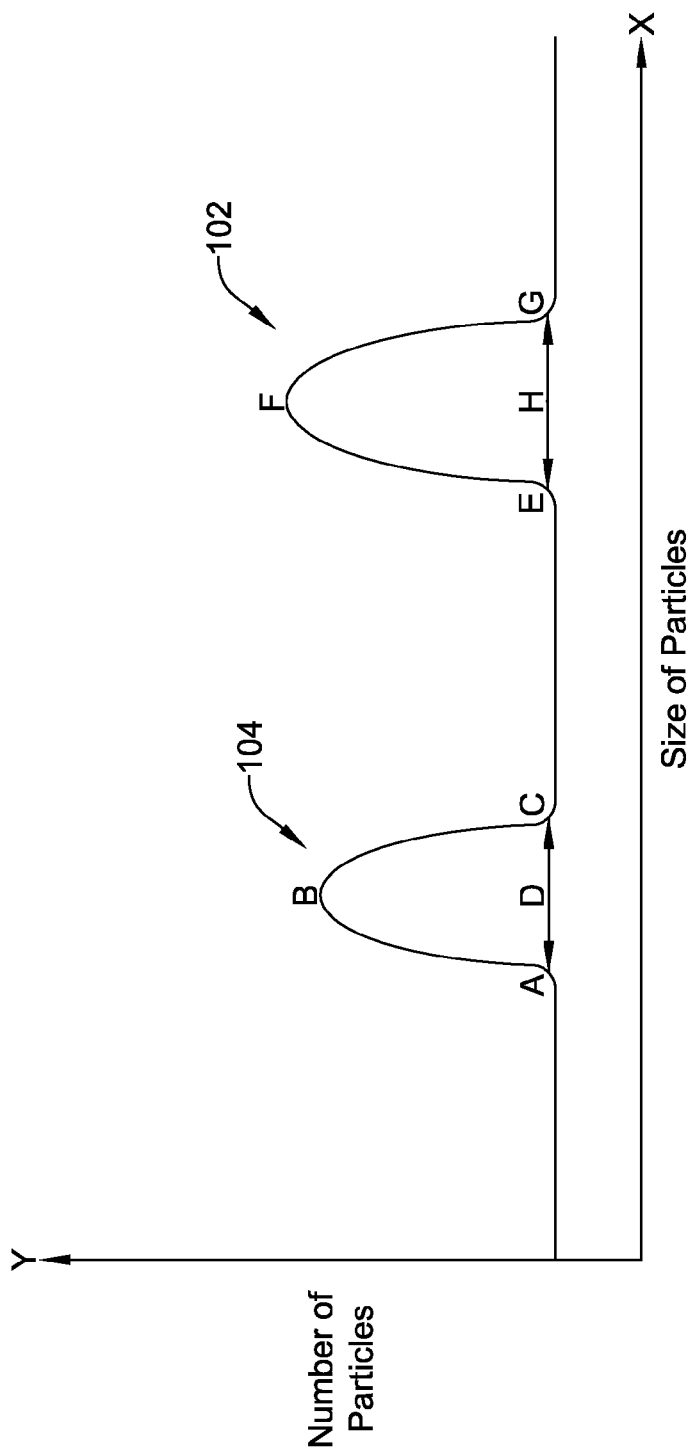
FIG. 2 is a schematic graphical view of an illustrative radiopaque material with a bimodal particle size distribution according to an aspect of this disclosure.

An illustrative example of a mixture that forms a bimodal distribution may include the situation where a first set of particles has a first normal distribution and a second set of particles have a second normal distribution, where the first and second normal distributions have the same standard deviation and the means of the first and second normal distributions differ by at least twice the common standard deviation. Other parameters may be set for determining if a mixture amounts to a multimodal particle size distribution, including, but not limited to, mixtures having two distinct modes, as shown in FIG. 2, mixtures having a set of particles with a mode that fits within interstitial spaces of one or more other sets of particles having a different particle size mode, and other similar or dissimilar parameters.

In some instances, the first set 102 of the radiopaque particles 101 and the second set 104 of the radiopaque particles 101 may be made from a single material type. The single material type can be a metal, an alloy, a salt, an oxide, or the like. Examples of such materials may include, but are not limited to tungsten, platinum, gold, tantalum, palladium, a salt made of tungsten, platinum, gold, or tantalum, or an oxide made of tungsten, platinum, gold, tantalum, or palladium, or combinations thereof, or the like. For example, the radiopaque particles may be made from tungsten, which is a material with a high density and a relatively high mass attenuation coefficient.

In some cases, the first set 102 of the radiopaque particles 101 and the second set 104 of the radiopaque particles 101 may be different types of materials. For instance, the first set 102 of the radiopaque particles 101 may be made from tungsten and the second set 104 of the radiopaque particles 101 may be made from a different material, such as tantalum or any other desirable material. In some instances, either or both of the two sets 102 and 104, or other sets, of the radiopaque particles 101 may have particles 101 of different types of material. For example, in the first set 102 of the radiopaque particles, 101 some of the particles 101 may be made from tungsten while the remaining particles 101 of the first set 102 are made from tantalum, or any other material, or any combination of materials, and in the second set 104 of the radiopaque particles, some particles may be made from gold while remaining particles of the second set 104 are made from palladium, any other radiopaque material, or any other combination of radiopaque materials.

The mixture formed by mixing the first set 102 of radiopaque particles 101 and the second set 104 of the radiopaque particles 101 may be mixed with material(s) typically used for medical devices. In at least some instances, the mixture of the radiopaque particles 101 in powder form may be mixed with powder, liquid, or other form of the material(s) used for making medical devices. The mixture of the radiopaque particles 101 may be turned into powder, if not already powder, through various methods including, but not limited to rod-milling.

When the mixture of the radiopaque particles 101 is in a powder, liquid, or other form, the mixture may undergo physical mixing with the material(s) used for making the medical device(s). The physical mixing method may involve mixing the two or more materials in any physical form such as liquid, solid (pulverized), molten, or the like, as desired. In some cases, mixing of the two or more materials (e.g., the radiopaque material 100 and the material of the medical device(s)) may involve chemical mixing. In some instances, radiopaque particles 101 of the mixture may be embedded into the material of the medical device. Illustratively, a mold having a cavity for receiving a molten form of the material of the medical device may be used to form the medical device with the mixture of radiopaque materials 100 and the material of the medical device, only the radiopaque material 100, or only the material of the medical device. Alternatively, or in addition, the radiopaque material 100 may be sprayed, laminated, coated, or the like on the medical device.

The medical device may be made from a biocompatible material. The biocompatible material may include polymer, metal, alloy, composite, or the like. Examples of such materials may include, but are not limited to silicone, polyurethane, nickel alloys, or the like.

Figure 6:
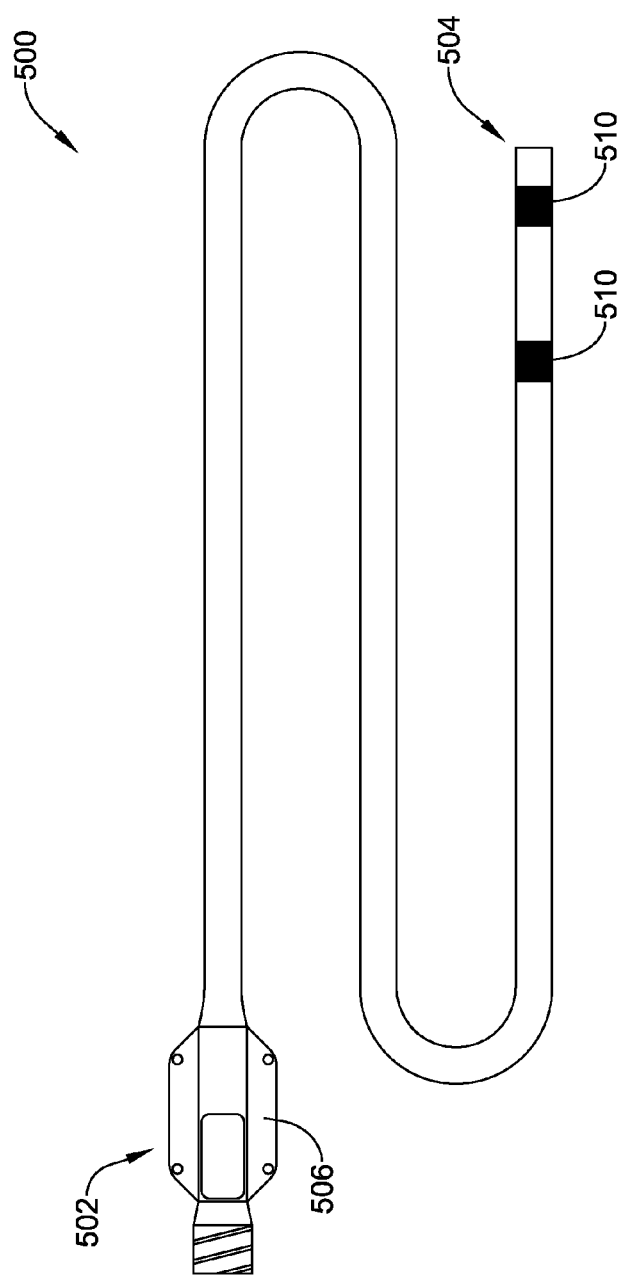
FIG. 6 is a schematic side view of an illustrative medical device having a marker according to an aspect of this disclosure.

In one aspect of the medical device, the first set 102 and the second set 104 of the radiopaque particles 101 may be arranged to form markers 510 on the medical device 500, as shown, for example, in FIG. 6. The markers 510 may have various forms, such as a band, a label, a ring, a coating, or the like, and can be disposed on a medical device at any position (e.g., at a distal end, a proximal end or any portion therebetween of a medical device).

It is contemplated that incorporation of the radiopaque material 100 into medical devices should be performed in such a way that it does not substantially affect or inhibit the performance of the medical device.

FIG. 2 is a schematic graphical representation of an illustrative radiopaque material 100 having two sets 102, 104 of radiopaque particles having particle size ranges D, H with distinct particle size modes B, F (e.g., a bimodal particle size distribution). Illustratively, a particle size may be a diameter, a radius, volume or other feature of a particle, but as generally discussed herein, the particle size of a particle may be the diameter of the particle. The radiopaque material 100 in FIG. 2 may include a first set 102 of radiopaque particles 101 and second set 104 of radiopaque particles 101. In FIG. 2, the size of the particles 101 is represented along the X-axis and the number of particles having a particle size is represented along the Y-axis. The two curves ABC and EFG depict particle size ranges and indicate that the most popular or common size of the particles 101 are represented by two local maxima—B and F (e.g., the modes of each set 102, 104 of radiopaque particles 101). "Local maxima" may refer to the points where the frequency stops increasing and begins decreasing. For instance, in the curve ABC, B is the local maxima (e.g., the mode) and in the curve EFG, F is the local maxima (e.g., the mode). Thus, B and F may be the two modes of the bimodal particle size distribution for the particles 101 of the first set 102 and the second set 104, respectively.

In some illustrative instances where the particle size is a measurement of a diameter of a particle 101, the mode of the second set 104 of radiopaque particles 101 may be substantially equal to or equal to 2.3 microns and the mode of the first set 102 of radiopaque particles 101 may be substantially equal to or equal to 7 microns. In a further illustrative instance where the particle size is a measurement of a diameter of a particle 101, the first set 102 of radiopaque particles 101 may have a particle size mode of 7 microns and 87% of the radiopaque particles 101 in a mixture and the second set 104 of the radiopaque particles 101 may have a particle size mode of 2.3 microns and 13% of the radiopaque particles 101 in the mixture.

Figure 3:
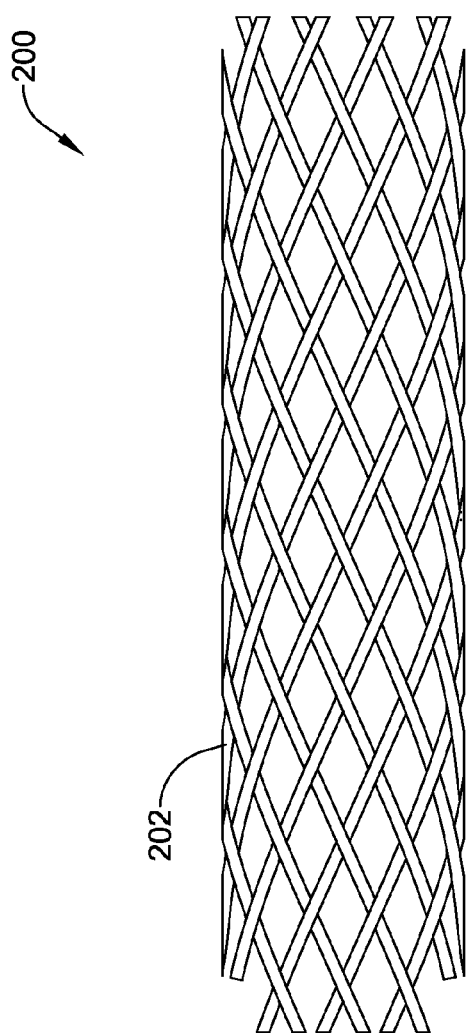
FIG. 3 is a schematic view of an illustrative medical device according to an aspect of this disclosure.

FIG. 3 is a schematic illustration of an illustrative stent 200 that may include a radiopaque material 100 having multiple sets of radiopaque particles 101 with different particle size ranges (e.g., a multimodal—bimodal, trimodal, etc. particle size distribution or other particle size distribution). The stent 200 may have a body 202 that is an elongated structure. In some instances, the stent 200 may be a mesh tube configured to be inserted into a vessel in a patient's body to prevent a disease-induced, localized flow constriction and/or inserted into a patient's body for any other purpose.

In some embodiments, the stent 200 having an elongated body structure 202 that may be at least partially formed from a biocompatible material, which may be loaded with the radiopaque particles 101. Here the term "loaded" may refer to the mixing or embedding of one material with or into at least one other material. Mixing and embedding of the two or more materials may refer to physical or chemical mixing or mixing in any other manner. In some of these and in other embodiments, the stent 200 may include one or more regions, structures, portions, or the like that include the radiopaque material 100.

After implantation in a patient's body, the stent 200 containing the mixture of the radiopaque particles 101 having multiple sets of particle size ranges may be monitored by X-ray scanning or fluoroscopy. In this manner, clear images of the stent 200 within the patient's body may be viewed.

In some instances, the radiopaque particles may be disposed over the stent 200 in the form of a marker (not shown). The marker may be disposed at the proximal end, the distal end, or both the proximal and the distal end of the stent 200.

Illustratively, the stent 200 may be a self-expandable stent. Self-expandable stents are well known in the art. Alternatively, the stent 200 may be a balloon-expandable stent. Balloon stents are well known in the art.

FIG. 4A shows a schematic illustration of an illustrative medical device that may be formed with a radiopaque material 100 having multiple sets of radiopaque particles 101 with different particle size ranges (e.g., a multimodal—bimodal, trimodal, etc. particle size distribution or other particle size distribution). The medical device depicted in FIG. 4A may be a guidewire 300 or other wire having an elongated structure with a substantially solid cross-section, as shown in FIG. 4B and taken along line B-B in FIG. 4A, and a proximal end 302 and a distal end 304. The guidewire 300 may be implanted in vasculature of a patient's body or other portion of the patient's body to act as a guide for other medical devices, including, but not limited to stents, catheters, etc. The guidewire 300 may be generally more flexible and steerable than other medical devices, as it may traverse through circuitous blood vessels or other anatomical lumens of the patient's body.

In some embodiments, the elongated structure of the guidewire 300 may be in the form of a wire, which may be formed with a biocompatible material that may be mixed with a radiopaque material 100. For example, the guidewire 300 may include a polymer that is loaded with the radiopaque material 100. The radiopaque material 100, which may include radiopaque particles 101 from two or more sets of particles having different particle size ranges (e.g., having a multimodal—bimodal, trimodal, etc.—particle size distribution or other particle size distribution), may be mixed with the material of the guidewire 300 to ensure effective attenuation of X-ray energy to produce high contrast images of the guidewire 300 in the human body. In some of these and in other embodiments, the guidewire 300 may include one or more regions, structures, portions, or the like that include the radiopaque material 100.

Figure 5A:
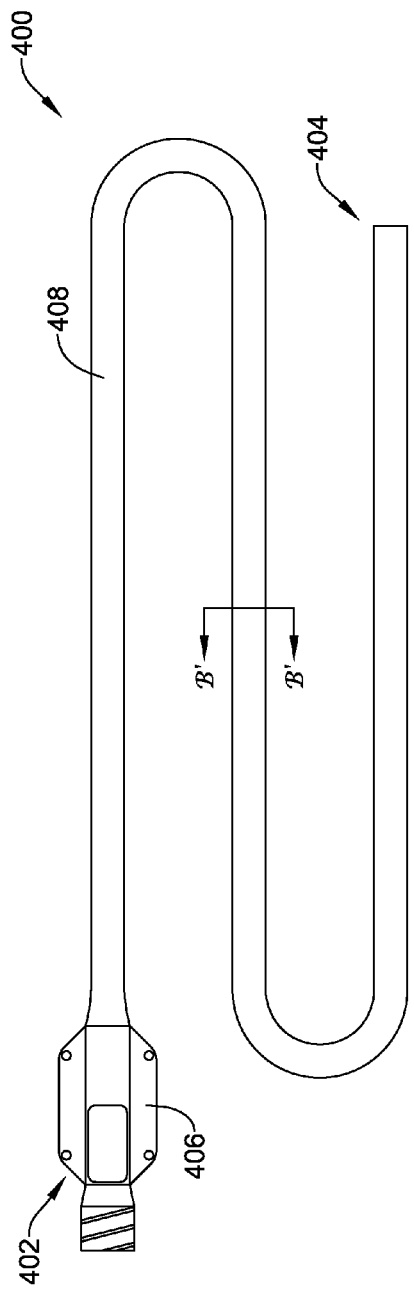
FIG. 5A is a schematic side view of an illustrative medical device according to an aspect of this disclosure.
Figure 5B:
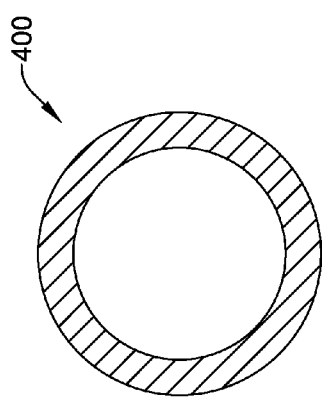
FIG. 5B is a schematic cross-sectional view of the illustrative medical device of FIG. 5A taken along line B'-B' according to an aspect of this disclosure.

FIG. 5A is a schematic illustration of an illustrative medical device that may be formed with a radiopaque material 100 having multiple sets of radiopaque particles 101 with different particle size ranges (e.g., a multimodal—bimodal, trimodal, etc. particle size distribution or other particle size distribution). The medical device depicted in FIGS. 5a and 5B may be a catheter 400. The catheter 400 may have an elongated structure or elongated shaft 408 that includes a proximal end 402 and a distal end 404. In some instances, the elongated structure or shaft 408 may be tubular, as shown in FIG. 5B and taken along line B'-B' of FIG. 5A. In some cases, a connector 406 may be disposed at the proximal end 402 of the catheter 400, which may be configured to connect to further medical devices, as desired. The distal end 404 of the catheter 400 may be placed inside a patient's body to assist in providing medical treatment to the patient.

The elongated structure of the catheter 400 may be made from a biocompatible material (e.g., a polymer or other material) that may be loaded with a radiopaque material 100. For example, the catheter 400 may include a polymer that is loaded with the radiopaque material 100. The radiopaque material 100 may include radiopaque particles 101 from two or more sets of particles having different particle size ranges (e.g., having a multimodal—bimodal, trimodal, etc.—particle size distribution or other particle size distribution). In some cases, the radiopaque material 100 may be mixed with a material of a catheter to ensure effective attenuation of X-ray energy to produce high contrast images of the catheter within the human body. A cross-sectional view of the catheter 400, taken along line B-B in FIG. 5A, is shown in FIG. 5B. In some of these and in other embodiments, the catheter 400 may include one or more regions, structures, portions, or the like that include the radiopaque material 100.

FIG. 6 is a schematic illustration of an illustrative medical device 500 having a proximal end 502 and a distal end 504 that has a marker 510 formed therein or positioned thereon. The marker 510 may be formed with a radiopaque material 100 having multiple sets of radiopaque particles 101 with different particle size ranges (e.g., a multimodal—bimodal, trimodal, etc. particle size distribution or other particle size distribution). The medical device 500 shown in FIG. 6 is a catheter that may be similar to the catheter 400 discussed with reference to FIG. 5A. In some instances, the marker 510 may be a separate member adapted to be disposed on any location of the medical device 500. Illustratively, the marker 510 may take the form of a coil, a ring, or any other form, as desired, that may be placed on or formed into the medical device 500. For example, the marker 510 may be disposed as a layer, band, adhesive, coating, ring, or other feature, on the medical device 500. Alternatively, or in addition, the marker 510 may make up an entirety of or a portion of the medical device 500. In some instances, the marker 510 may be integral with, a portion of, joined with, and/or joined to in direct contact with, the medical device 500.

The marker 510 may include radiopaque particles 101 from two or more sets of particles having different particle size ranges (e.g., having a multimodal—bimodal, trimodal, etc.—particle size distribution or other particle size distribution) to ensure effective attenuation of X-ray energy to produce high contrast images of locations of the markers 510 on the medical device 500 (e.g., a catheter, guidewire, etc.).

In some instances, the marker 510 may be fixed on a catheter using sealing adhesives, such as 3-aminopropyltrimethoxysilane, or the like. Alternatively, or in addition, the marker 510 may be affixed to the catheter 500 by a snap-fit mechanism, slit-fit mechanism, by a welding technique, or through any other connection mechanism and/or technique, as desired.

Although stents, guidewires, and catheters, are specifically discussed in this disclosure, such medical devices are merely illustrative. Persons skilled in the art may contemplate incorporating the radiopaque material 100 discussed herein into other medical devices such as stent-grafts, vascular grafts, tubular implantable medical devices, etc.

Figure 7:
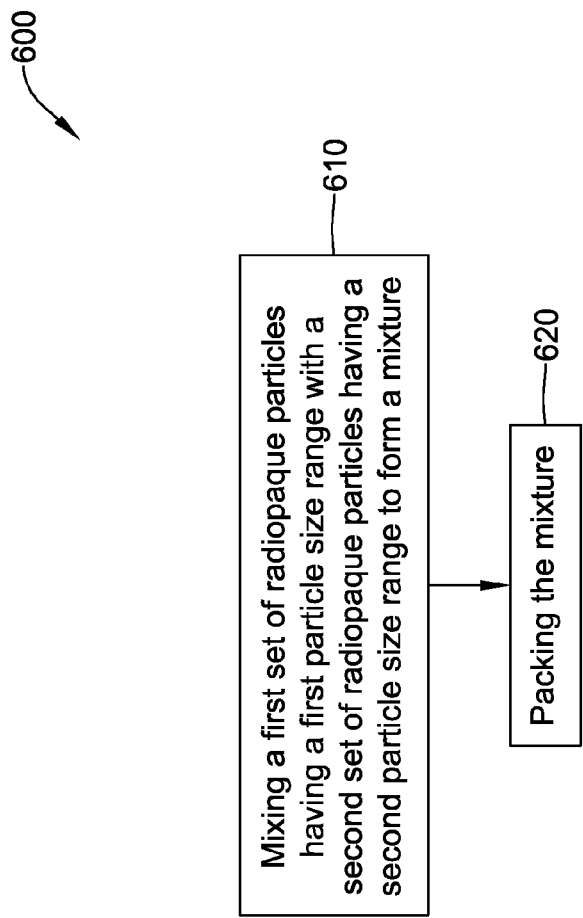
FIG. 7 is a schematic flow diagram of an illustrative method of forming a radiopaque material according to an aspect of this disclosure.

In one aspect, as depicted in FIG. 7, a method 600 of manufacturing a radiopaque material 100 for a medical device is disclosed which includes selecting one or more types of radiopaque material and mixing 610 a first set 102 of radiopaque particles 101 of one or more of the selected one or more types of radiopaque material with a second set 104 of the radiopaque particles 101 of one or more of the selected one or more types of radiopaque material. In some instances, the first set 102 of radiopaque particles 101 may have a first particle size range with particle sizes generally larger than particle sizes of particles 101 in the second set 104 of particles 101 having a second range of particle sizes.

Then, in some cases, once the first set 102 of radiopaque particles 101 has been mixed with the second set 104 of radiopaque particles 101, the mixed particles, optionally, may be packed 620 together to obtain a closer packing of particles 101 and improve the density of the mixed material. Illustratively, the mixture of radiopaque particles 101 may be packed through any packing technique. For example, the mixture of radiopaque particles 101 may be packed by applying ultrasonic energy to the mixture of the first set 102 of the radiopaque particles 101 and the second set 104 of the radiopaque particles 101, by applying mechanical vibration to the mixture of the first set 102 of the radiopaque particles 101 and the second set 104 of the radiopaque particles 101, and/or by applying other packing techniques to the mixture of the first set 102 of the radiopaque particles 101 and the second set 104 of the radiopaque particles 101, as desired.

Further, in some cases, the mixed (and optionally packed) radiopaque material 100 having multiple sets of radiopaque particles 101 may be mixed with and/or applied to the material of a medical device. Such mixing and/or applying may be executed in any mixing and/or application manner, as desired.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A medical device, comprising:
an elongated structure including a radiopaque material; and
wherein:
the radiopaque material comprises a first set of radiopaque particles having a first particle size mode and a second set of radiopaque particles having a second particle size mode that is approximately 10%-35% of the size of the first particle size mode;
the first set of radiopaque particles have a particle size distribution in the range of about 6 microns to about 12 microns;
the second set of radiopaque particles have a particle size distribution in the range of about 0.7 microns to about 4 microns;
the radiopaque material comprises 70%-90% by weight of the first set of radiopaque particles and 10%-30% by weight of the second set of radiopaque particles; and
particle sizes of individual particles of the second set of radiopaque particles are configured such that the individual particles of the second set of radiopaque particles fit in interstitial spaces between individual particles of the first set of radiopaque particles.

2. The medical device of claim 1, wherein the radiopaque particles of the first set of radiopaque particles and the second set of radiopaque particles are made from a single material type.

3. The medical device of claim 2, wherein the single material type is tungsten.

4. The medical device of claim 2, wherein the single material type is a metal material.

5. The medical device of claim 2, wherein the single material type is one of tungsten, platinum, gold, tantalum, palladium, a salt made of tungsten, platinum, gold, tantalum, or palladium, or an oxide made of tungsten, platinum, gold, tantalum, or palladium.

6. The medical device of claim 1, wherein:
the first set of radiopaque particles have a particle size distribution, where the first particle size mode is about 7 microns; and
the second set of radiopaque particles have a particle size distribution, where the second particle size mode is about 2.3 microns.

7. The medical device of claim 1, wherein:
the first set of radiopaque particles have a first particle size distribution having a first range of particle sizes; and
the second set of radiopaque particles have a second particle size distribution having a second range of particle sizes with particles sized about 10%-35% of particle sizes of the first range of particle sizes.

8. The medical device of claim 1, wherein the radiopaque material comprises:
about 87% by weight of the first set of radiopaque particles; and
about 13% by weight of the second set of radiopaque particles.

9. The medical device of claim 8, wherein:
the first particle size mode is about 7 microns; and
the second particle size mode is about 2.3 microns.

10. A medical device, comprising:
a structure including a radiopaque material;
wherein:
the radiopaque material comprises 70%-90% by weight of a first set of radiopaque particles having a first particle size mode and 10%-30% by weight of a second set of radiopaque particles having a second particle size mode that is approximately 10%-35% of the size of the the first particle size mode;
the first set of radiopaque particles have a particle size distribution in the range of about 6 microns to about 12 microns;
the second set of radiopaque particles have a particle size distribution in the range of about 0.7 microns to about 4 microns; and particle sizes of individual particles of the second set of radiopaque particles are configured such that the individual particles of the second set of radiopaque particles fit in interstitial spaces between individual particles of the first set of radiopaque particles.

11. The medical device of claim 1, wherein the elongated structure comprises a composition including a polymer and the radiopaque material.

12. The medical device of claim 1, wherein the radiopaque material is arranged to form a marker for the elongated structure.

13. The medical device of claim 1, wherein the elongated structure is a tubular member.

14. The medical device of claim 1, wherein the elongated structure is in the form of a wire.

15. The medical device of claim 1, wherein the elongated structure is in the form of a stent.

16. A medical device, comprising:
a structure including a radiopaque material;
wherein the radiopaque material comprises 70%-90% by weight of a first set of radiopaque particles having particle sizes within a first range of particle sizes and 10%-30% by weight of a second set of radiopaque particles having particle sizes within a second range of particle sizes;
wherein the first range of particle sizes is 6 microns to 12 microns;
wherein the second range of particle sizes is 0.7 microns to 4 microns.

* * * * *